United States Patent [19]

Bogue et al.

[11] 4,270,535
[45] Jun. 2, 1981

[54] DOUBLE LUMEN CATHETERS

[75] Inventors: Beuford A. Bogue, Littleton, Colo.; Stephan A. Gagneux, Muttenz, Switzerland

[73] Assignee: Hospal Medical Corp., Littleton, Colo.

[21] Appl. No.: 86,043

[22] Filed: Oct. 18, 1979

[51] Int. Cl.³ ............................................. A61M 5/14
[52] U.S. Cl. ................................. 128/214.4; 128/221; 128/347
[58] Field of Search ............. 128/214.4, 214.2, 214 R, 128/221, 347, 349, 350, DIG. 16, 240

[56] References Cited

U.S. PATENT DOCUMENTS

| 3,572,334 | 3/1971 | Petterson | 128/214.4 |
| 3,833,003 | 9/1974 | Tarrico | 128/347 |
| 4,073,297 | 2/1978 | Kopp | 128/214.4 |
| 4,202,332 | 5/1980 | Tersteegen et al. | 128/214.4 |

Primary Examiner—Stephen C. Pellegrino
Attorney, Agent, or Firm—Gerald D. Sharkin; Robert S. Honor; Walter F. Jewell

[57] ABSTRACT

A double lumen, single needle, catheter is provided having an improved insertion tip which aleviates the trauma induced when inserted in a blood vessel or fistula.

7 Claims, 3 Drawing Figures

DOUBLE LUMEN CATHETERS

BACKGROUND OF THE INVENTION

This invention relates to catheters. More particularly, the invention relates to double lumen catheters for placement in an artery, vein or fistula vessel of a patient, through which blood may be withdrawn and delivered simultaneously to and from the patient's blood or body fluid access.

Two important medical problems arise when large blood flows have to be established for relatively long time periods when using catheters. The first is trauma to the blood vessel or fistula due to the catheter insertion. The second is the possibility of additional vessel trauma as a result of movements of the sharp catheter tip lodged within the vessel. This invention provides a double lumen catheter which aleviates the above blood vessel or fistula trauma.

SUMMARY OF THE INVENTION

Broadly, this invention provides an improved double lumen single needle intravenous catheter device having a hub means including first and second spaced apart fluid conduit means, with an inner lumen in fluid communication at its proximal end with the first conduit means and an outer lumen in fluid communication at its proximal end with the second conduit means, the lumens being in concentric relationship to one another. At least one aperature is provided in the wall of the outer lumen at its distal end region.

The improvement comprises a substantially frustroconical tip element of plastics material having a bore defining an extension of the inner lumen and having an annular base section providing an annular seal between the outer surface of the distal end region of the inner lumen and the adjacent interior surface of the distal end region of the outer lumen.

This structure defines an annular passage between the inside surface of the outer lumen and the outside surface of the inner lumen which communicates between the aperature and the second conduit means and which is sealed from the passage provided by the bore of the tip element and the inner lumen which communicates with the first conduit means. The substantially frustroconical surface of the tip element provides for ease of entry of the catheter into a blood vessel or fistula.

In one aspect of the invention, the distal end of the outer lumen may be recessed in the peripheral surface of the base portion of the tip.

In a preferred embodiment of the catheter of this invention, the distal end of the outer lumen has an annular inwardly directed flange which mates with a corresponding recess in the base portion of the tip to secure the tip in fluid-tight relationship with the inner and outer lumens.

The distal end region of the inner lumen may be fitted into a recesss in the bore of the tip so as to provide a substantially continuous smooth fluid passage from the interior of the inner lumen to the opening defined by the bore at the end of the tapered portion of the tip. The distal ends of the inner and outer lumens may be in substantial alignment.

The catheter of this invention may have a removable trocar located in the inner lumen such that the point of the trocar protrudes through the opening defined by the distal end of the inner lumen and beyond the tapered portion of the tip. The first conduit means may have a flexible tube coaxially connected to its free end and a removable resealable plug sealing closed the free end of the flexible tube.

The tip of the catheter of this invention may be prepared from plastic material. Preferably the plastic should have a low coefficient of surface friction to allow for ease of insertion of the catheter following penetration of the blood vessel or fistula of a patient by the trocar. Preferred plastic materials are polyethylene, silicone, polyvinylchloride, teflon, e.g., polytetrafluoroethylene and the like. Teflon and polyethylene are the most preferred.

DETAILED DESCRIPTION

Figure 1:
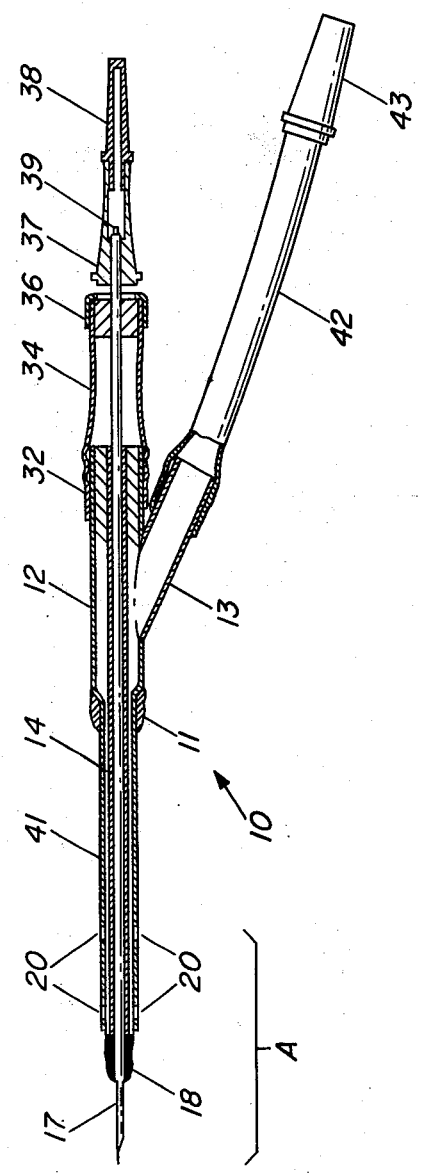
FIG. 1 is a cross-sectional side elevation of a catheter assembly having inner and outer lumens in concentric relationship to one another and a removable trocar passing through the inner lumen.

Referring to FIG. 1, reference numeral 10 refers generally to a prior art double lumen catheter assembly having a hub 11 connected to a first conduit 12 and a second conduit 13. An inner lumen 14 is coaxially connected to the first conduit and an outer lumen 16 is coaxially connected to the second conduit. Both the inner and outer lumens are in concentric relationship to one another. A removable trocar 17 is shown disposed within the inner lumen 14.

Figure 2:
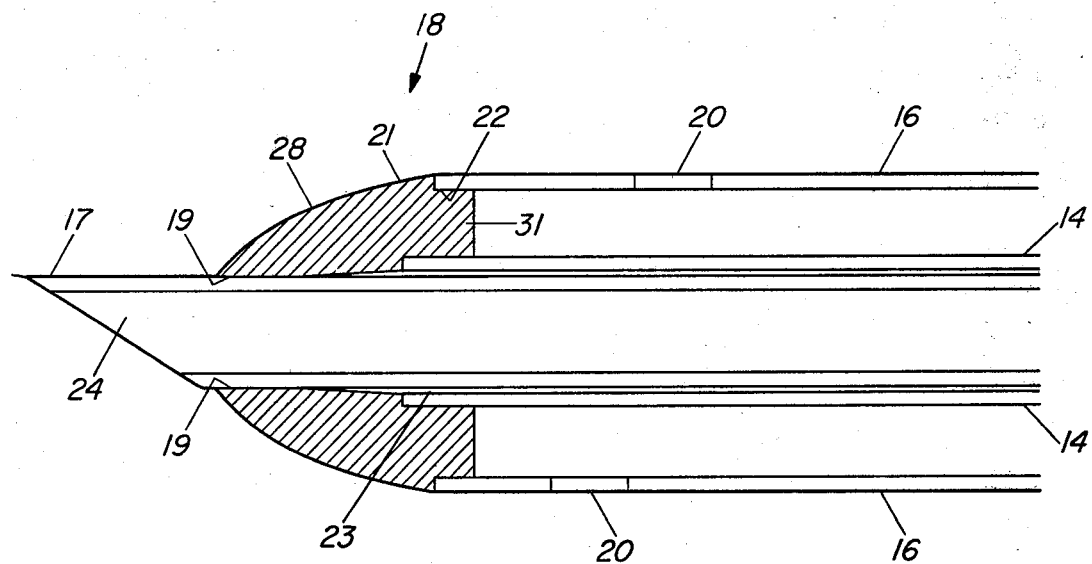
FIG. 2 is a cross-sectional side elevation of the area A of the catheter of FIG. 1 showing a catheter tip of this invention.

A plastic tip 18 of this invention (shown in detail in FIG. 2 and FIG. 3) has a bore 19 disposed about the inner lumen 14 in a fluid tight relationship. Oposed aperatures 20 are provided in the wall of the outer lumen 16 in the distal end region proximal to the tip 18. The peripheral surface 21 of the tip is in fluid sealing engagement with the adjacent interior surface 22 of the outer lumen 16. As shown in FIG. 2, the outer lumen 16 is recessed at its distal end region in the peripheral surface 21 of the tip to a depth that corresponds substantially to the thickness of the lumen wall. This provides a substantially uninterrupted surface between the surface (periphery) of the tip 18 and the outer lumen 16.and allows for ease of entry of the catheter 10 into a blood vessel or fistula without undue trauma to the vessel or fistula.

Similarly, the inner lumen 14 is recessed within the bore 19 to a depth equal to the lumen thickness. This provides a substantially continuous level annular fluid (e.g., blood) passage from the interior 23 of the inner lumen 14 to the opening 24 of the bore 19.

Figure 3:
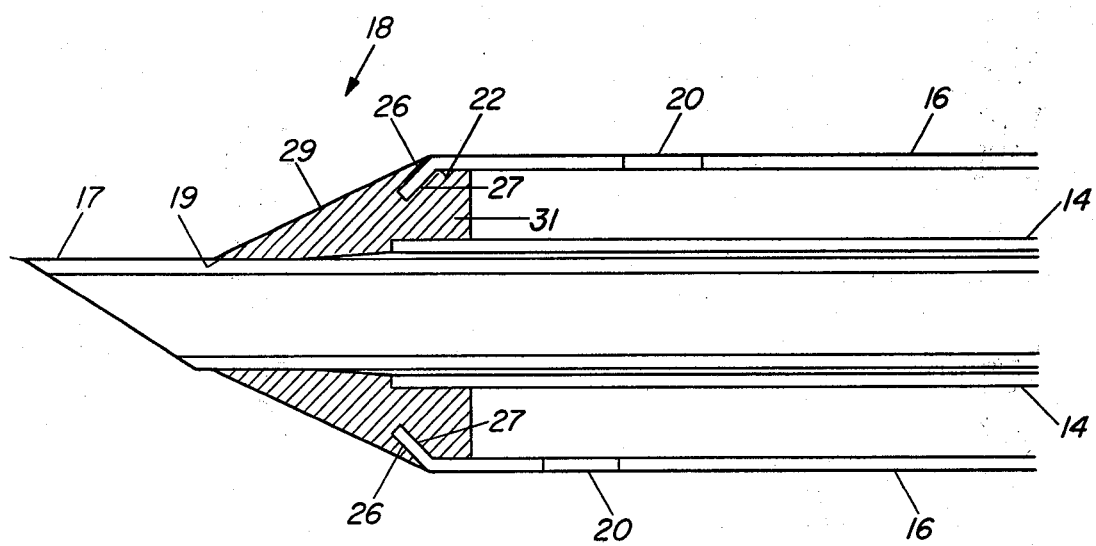
FIG. 3 is a cross-sectional side elevation of a preferred catheter tip of this invention.

Referring to FIG. 3, there is shown a preferred embodiment of the catheter tip 18 of this invention. An annular flange 26 at the distal end of the outer lumen 16 is provided. This flange mates with a corresponding recess 27 in the tip to secure the tip to the catheter. An additional feature set forth in FIG. 2 and FIG. 3 is the tapered shape 28 in FIG. 2 and the conical shape 29 of the tip in FIG. 3. In both FIG. 2 and FIG. 3, the tip has a substantially cylindrical base portion 31 which is in sealing relationship with the inner and outer lumens with the tapered portion 28 and the conical portion 29 extending from the base portion 31.

The catheter 10 may be conventionally provided with a fluid seal 32 having a bore 33 in which the proximal end of the inner lumen 14 is sealingly engaged. The bore 33 and inner lumen 14 are in fluid communication with a flexible tube 34. Tube 34 has a removable plug 36 through which the trocar 17 passes.

A female luer 37 is mounted at the proximal end of the trocar 17 which is kept closed by a removable closure cap 38. The female luer has a bore 39 into which an infusion syringe may be fitted.

In operation, the vein, artery or fistula vessel is punctured by means of the trocar 17 and the catheter is inserted into the vessel to a point near the proximal end region 41. Infusion may be effected through the trocar 17 during this placement. The trocar is then withdrawn, the flexible tube 34 clamped closed, the removable resealable plug 36 removed and the end of the flexible tube 34 connected up to a blood line leading to a monitoring and blood pump device (not shown). Similarly, a short length of flexible tubing 42 connected to the second conduit 13 is clamped closed, a cap 43 removed and connected up to a blood line leading from the monitoring and blood pump device.

What is claimed is:

1. In a double lumen single needle intraveneous catheter device having a hub means including first and second spaced apart fluid conduit means, an inner lumen in fluid communication at its proximal end with the first conduit means, an outer lumen in fluid communication at its proximal end with the first conduit means, an outer lumen in fluid communication at its proximal end with the second conduit means the lumens being in concentric relationship to one another, at least one aperature being provided in the wall of the outer lumen at its distal end region, the improvement which comprises a substantially frustroconical tip element of plastics material having a bore defining an extension of the inner lumen and having an annular base section providing an annular seal between the outer surface of the distal end region and the inner lumen and the adjacent interior surface of the distal end region of the outer lumen, wherein the distal end of the outer lumen has an inwardly directed annular flange which mates with a corresponding recess in the base portion of the tip to secure the tip in fluid tight relationship with the inner and outer lumens, whereby an annular passage is defined between the inside surface of the outer lumen and the outside surface of the inner lumen which communications between the aperature and the second conduit means and which is sealed from the passage provided by the bore of the tip element and the inner lumen which communicates with the first conduit means, and whereby the substantially frustroconical surface of the tip element provides for ease of entry of the catheter into a blood vessel or fistula.

2. The catheter device of claim 1 wherein the distal end region of the inner lumen is recessed in the bore of the tip so as to provide a substantially continuous smooth fluid passage from the interior of the inner lumen to the opening defined by the bore at the end of the tapered portion of the tip.

3. The catheter device of claim 2 wherein the distal ends of the inner and outer lumens are in substantial alignment.

4. The catheter device of claim 2 wherein the plastic tip is polytetrafluoroethylene.

5. The catheter device of claim 3 wherein the plastic tip is polyethylene.

6. The catheter device of claim 1 wherein a removable trocar is located in the inner lumen so that the point of the trocar protrudes through the opening defined by the distal end of the inner lumen and beyond the tapered portion of the tip.

7. The catheter device of claim 1 wherein the first conduit means has a flexible tube coaxially connected to its free end and a removable resealable plug sealing closed the free end of the flexible tube and through which the removable trocar passes.

* * * * *